United States Patent [19]

Keogh et al.

[11] Patent Number: 5,675,007
[45] Date of Patent: Oct. 7, 1997

[54] DERIVATIVES OF QUINUCLIDINE N-OXIDE AS MUSCARINIC RECEPTOR LIGANDS

[75] Inventors: John Keogh, Hitchin; Gary Thomas Borrett, Bishops Stortford; Steven Mark Bromidge, Sawbridgeworth; Erol Ali Faruk, Enfield; Mark Jason Hughes, Welwyn; John Kitteringham, Hertford; Martyn Voyle, Welwyn, all of United Kingdom

[73] Assignee: SmithKline Beecham p.l.c., Brentford, United Kingdom

[21] Appl. No.: 737,424

[22] PCT Filed: May 9, 1995

[86] PCT No.: PCT/EP95/01758

§ 371 Date: Nov. 12, 1996

§ 102(e) Date: Nov. 12, 1996

[87] PCT Pub. No.: WO95/31457

PCT Pub. Date: Nov. 23, 1995

[30] Foreign Application Priority Data

May 14, 1994 [GB] United Kingdom ............. 9409718

[51] Int. Cl.[6] .......... C07D 211/94; C07D 221/22; A61K 31/435
[52] U.S. Cl. .............. 546/133; 514/305
[58] Field of Search ............ 546/133; 514/305

[56] References Cited

U.S. PATENT DOCUMENTS 5,278,170  1/1994  Orlek et al. .............. 514/304

FOREIGN PATENT DOCUMENTS 0 392 803  10/1990  European Pat. Off. ...... C07D 453/02

*Primary Examiner*—C. Warren Ivy
*Assistant Examiner*—Charanjit S. Aulakh
*Attorney, Agent, or Firm*—Linda E. Hall; Stephen A. Venetianer; Edward T. Lentz

[57] ABSTRACT

A compound of formula (I) or a pharmaceutically acceptable salt thereof (I) wherein $R_1$ represents (a), $R_2$ is a group $OCH_3$, and $R_3$ is cyano, for use in the treatment and/or prophylaxis of dementia in mammals.

11 Claims, No Drawings

DERIVATIVES OF QUINUCLIDINE N-OXIDE AS MUSCARINIC RECEPTOR LIGANDS

This application is the U.S. National phase of PCT/EP95/01758 filed May 9, 1995; published as WO95/31457 on Nov. 23, 1995.

This invention relates to a compound having pharmaceutical activity, to a process for its preparation and its use as a pharmaceutical.

EP-A-0392803 (Beecham Group p.l.c.) discloses certain azabicyclic compounds which enhance acetylcholine function via an action at muscarinic receptors within the central nervous system, including (±)α-(methoxyimino)-α-(1-azabicyclo[2.2.2]oct-3-yl)acetonitrile and its enantiomers.

A novel compound has now been discovered which also enhances acetylcholine function via an action at muscarinic receptors within the central nervous system and is therefore of potential use in the treatment and/or prophylaxis of dementia in mammals.

According to the present invention, there is provided a compound of formula (I) or a pharmaceutically acceptable salt thereof.

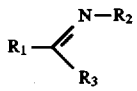
(I)

wherein $R_1$ represents

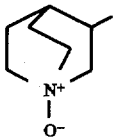

$R_2$ is a group $OCH_3$, and $R_3$ is cyano.

The compound of formula (I) is capable of existing in a number of stereoisomeric forms including geometric isomers such as E and Z and enantiomers. The invention extends to each of these stereoisomeric forms, and to mixtures thereof (including racemates). The different stereoisomeric forms may be separated one from the other by the usual methods, or any given isomer may be obtained by stereospecific or asymmetric synthesis.

The compound of formula (I) is preferably in pharmaceutically acceptable form. By pharmaceutically acceptable form is meant, inter alia, of a pharmaceutically acceptable level of purity excluding normal pharmaceutical additives such as diluents and carriers, and including no material considered toxic at normal dosage levels. A pharmaceutically acceptable level of purity will generally be at least 50% excluding normal pharmaceutical additives, preferably 75%, more preferably 90% and still more preferably 95%. One preferred pharmaceutically acceptable form is the crystalline form, including such form in a pharmaceutical composition.

The compound of formula (I) can form acid addition salts with strong acids. The term pharmaceutically acceptable salt encompasses solvates and hydrates. Thus, where the compound of formula (I) or pharmaceutically acceptable salts thereof forms solvates or hydrates, these also form an aspect of the invention.

The invention also provides a process for the preparation of the compound of formula (I), or a pharmaceutically acceptable salt thereof, which process comprises:

(a) reacting a compound of formula (II):

(II)

with a compound of formula (III):

(III)

wherein $R_2'$ represents $R_2$ or hydroxy, and $R_1'$ and $R_3'$ represent $R_1$ and $R_3$ or groups convertible thereto, and thereafter converting $R_2'$ to $R_2$ when hydroxy, and converting $R_1'$ and $R_3'$ when other than $R_1$ and $R_3$ to $R_1$ and $R_3$, wherein $R_1$, $R_2$ and $R_3$ are as defined in formula (I);

(b) reacting a compound of formula (IV):

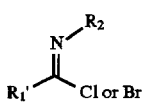
(IV)

wherein $R'_1$ is $R_1$ or a group convertible thereto, with a compound of formula (V):

(V)

capable of generating an $R_3$ nucleophile, and thereafter converting $R_1'$ when other than $R_1$ to $R_1$, wherein $R_1$, $R_2$ and $R_3$ are as defined in formula (I);

(c) nitrosating a compound of formula (VI):

(VI)

wherein $R_1'$ is $R_1$ or a group convertible thereto, and $R_3''$ is an electron withdrawing group, and thereafter converting the resulting =NOH group to =NR$_2$ and converting $R_1'$ and $R_3''$ when other than $R_1$ and $R_3$ to $R_1$ and $R_3$, wherein $R_1$, $R_2$ and $R_3$ are as defined in formula (I);

(d) reacting a compound of formula (X):

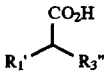
(X)

wherein $R_1'$ is $R_1$ or a group convertible thereto, and $R_3''$ is an electron withdrawing group, with a source of nitrous acid and thereafter converting the resulting =NOH group to =NR$_2$ and converting $R_1'$ and $R_3''$ when other than $R_1$ and $R_3$ to $R_1$ and $R_3$, wherein $R_1$, $R_2$ and $R_3$ are as defined in formula (I); or (e) oxidising a compound of formula (VII):

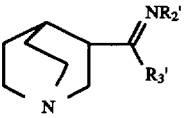
(VII)

wherein $R_2'$ and $R_3'$ are $R_2$ and $R_3$ or groups convertible thereto and thereafter converting $R_2'$ and $R_3'$ when other than $R_2$ and $R_3$ to $R_2$ and $R_3$ as defined in formula (I); and thereafter optionally forming a pharmaceutically acceptable salt.

Conversion of $R_1'$, $R_2'$, $R_3'$ and $R_3''$ may take place in any convenient order.

The reaction between the compounds of formulae (II) and (III) (reaction variant (a)) is preferably carried out in a hydroxylic solvent such as methanol or ethanol, at ambient temperature, or where appropriate, at elevated temperature.

In the compound of formula (III) $R_2'$ is conveniently $R_2$.

The reaction between compounds of formulae (IV) and (V) (reaction variant (b)) may be carried out under standard conditions for the displacement of halogen by a nucleophile. The residue M is suitably an alkali metal such as sodium or lithium, preferably (V) is NaCN, and the reaction is conveniently carried out at elevated temperature in an inert solvent such as dimethyl sulphoxide or methanol.

Compounds of formula (II) and (IV) may be prepared as described in EP-A-0392803.

In reaction variants (c) and (d), examples of suitable electron withdrawing groups in the compounds of formulae (VI) and (X) include CN, $CO_2R$ and $CON(R)_2$ in which each R is independently H, $C_{1-8}$ alkyl, $C_{2-8}$ alkenyl, $C_{2-8}$ alkynyl, $C_{3-8}$ cycloalkyl, $C_{3-8}$ cycloalkyl $C_{1-4}$ alkyl or aryl $C_{1-4}$ alkyl, wherein aryl groups are selected from optionally substituted phenyl and naphthyl. Suitable examples of substituents on phenyl and naphthyl include one or more, for example 1 to 3, substituents selected from halo, hydroxy, $C_{1-4}$ alkoxy and $C_{1-4}$ alkyl. $R_3''$ is preferably CN.

The nitrosation of the compound of formula (VI) may be carried out using a nitrosating agent such as an alkylnitrite, preferably a $C_{1-8}$ alkylnitrite such as t-butyl nitrite or, more preferably, iso-amyl nitrite and a base such as sodium ethoxide or, more preferably, potassium t-butoxide. Dimethyl sulphoxide (DMSO) and tetrahydrofuran (THF) are suitable examples of solvents for the nitrosation.

The nitrosation results in a compound of formula (VIII):

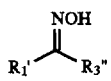

(VIII)

The =NOH group of the oxime of formula (VIII) may be convened to =NR$_2$ by conventional routes, for example by alkylation with an alkylating agent such as methyl tosylate (methyl p-toluene sulphonate) or an alkyl halide, for example methyl iodide. The alkylation is preferably carried out at a temperature of −20° C.–40° C., more preferably 0° C.–40° C., for example 18° C.–36° C., most preferably below 35° C., and is preferably preceded by treatment of oxime of formula (VIII) with base such as potassium t-butoxide.

The compound of formula (X) may be provided in the form of an ester hydrolysed to the free acid prior to reaction with the source of nitrous acid.

The reaction of the compound of formula (X) with the source of nitrous acid, for example an alkali metal nitrite such as sodium nitrite may be carried out in aqueous acid such as hydrochloric acid for example at 0° C. to 50° C.

After basification, the reaction results in a compound of formula (VIII). When $R_1'$ is a 1-azabicyclo[2.2.2.]oct-3-yl group and $R_3''$ is CN, the Z isomer of the compound of formula (VIII) may be crystallised out from the reaction mixture in the zwitterionic form.

The =NOH group of the oxime of formula (VIE) may be converted to =NR$_2$ as described above.

$R_3''$ groups other than CN may be convened thereto conventionally, for example conversion, if necessary, to the primary amide followed by dehydration.

Examples of $R_1'$ groups other than 1-azabicyclo[2.2.2] oct-3-yl and $R_1$ include suitable azacyclic precursors which may be cyclised as described in, for example, EP 0392803.

Conversion of an $R_1'$ 1-azabicyclo[2.2.2]oct-3-yl group to $R_1$ is preferably carried out as the final step, corresponding to reaction variant (e), by conventional oxidation using an oxidising agent such as m-chloroperoxybenzoic acid (G. L. Kenyon et al, J. Org. Chem., 1976 41 2417, J. Cymerman Craig et al, J. Org. Chem., 1970 35 1721) in an inert solvent such as dichloromethane at depressed temperature, or hydrogen peroxide (K. Naumann et al, J. Amer. Chem. Soc., 1969 91 7012).

Compounds of formula (VI) can be prepared from compounds of formula (IX):

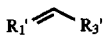

(IX)

by hydrogenation according to standard procedures as described in WO 93/17018.

A process for preparing a compound of formula (VIII) comprises reacting a compound of formula (X) with a source of nitrous acid such as an alkali metal nitrite and thereafter optionally converting $R_1'$ and $R_3'$ when other than $R_1$ and $R_3$ to $R_1$ and $R_3$ and thereafter optionally forming a salt.

Compounds of formula (X) can be prepared from corresponding compounds of formula (XI) or esters thereof:

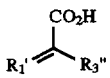

(XI)

by hydrogenation according to standard procedures optionally followed by ester hydrolysis and conversion of $R_1'$ and $R_3'$ to $R_1$ or 1-azabicyclo[2.2.2]oct-3-yl, or CN respectively.

The reduction of compounds of formula (XI) and their esters is preferably carried out by treating a solution of a compound of formula (XI) or ester with hydrogen under atmospheric or elevated pressure, in the presence of a precious metal catalyst such as Palladium on carbon. The resulting compound of formula (X) may be isolated or alternatively the reaction product may be used directly in the reaction with the source of nitrous acid.

Compounds of formula (X) are novel.

Compounds of formula (XI) may be prepared by reacting 3-quinuclidinone with a compound $R_3'CH_2CO_2H$ or the ester, optionally followed by conversion of $R_1'$ and/or $R_3'$ to $R_1$ or CN respectively.

The reaction of 3-quinuclidinone may be carried out in aqueous base, such as sodium hydroxide at moderate temperatures, for example ambient to 50° C.

Where the $R_3'$ group is a carboxy derivative such as an alkoxycarbonyl group, it may be converted to a cyano group by conventional methods as described above, but preferably before hydrogenation or the reaction with alkali metal nitrite.

However, as stated above, $R_3'$ is preferably cyano and no conversion is necessary.

Compounds of formula (III) are known compounds or may be prepared by analogous methods to those for preparing known compounds. Certain compounds of formula (III) are commercially available.

The compounds of formula (VII) may be prepared by conventional routes such as described in EP 0392803 and WO 93/17018, for example by reaction variants (a), (b) or (c) above in which $R_1'$ is 3-quinuclidinyl. Alternatively the compounds of formula (VII) where $R_2'$ and $R_3'$ are $R_2$ and $R_3$ may be prepared by reacting a compound of formula (IVa)

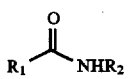

(IVa)

wherein $R_1'$ is 3-quinuclidinyl, with a chlorinating or brominating agent and thereafter convening the resulting chloro or bromo group to $R_3$;

For the reaction of compounds of formula (IVa) with a chlorinating or, brominating agent, suitable chlorinating agents include phosphorus pentachloride which undergoes reaction in nitromethane at reduced temperature, for example 0° C., and dichlorotriphenylphosphine (carbon tetrachloride/triphenyl phosphine) which undergoes reaction in acetonitrile at elevated temperature, for example at the boiling point of the solvent. Suitable brominating agents include dibromotriphenylphosphine (carbon tetrabromide/ triphenylphosphine) which undergoes reaction in acetonitrile at elevated temperature, for example at the boiling point of the solvent.

Conversion of the resulting chloro or bromo group to $R_3$ may be effected by reaction variant (b) above. Compounds of formula (IVa) may be prepared as described in EP-A-0392803.

The different stereoisomeric forms of compounds of formula (I) may be separated one from the other by the usual methods, for example using chromatographic methods or during treatment of the compound of formula (I) or earlier intermediates such as of formulae (VII) or (VIII) with chiral resolving agents. Alternatively, any given isomer may be obtained by stereospecific or asymmetric synthesis. Resolution is preferably carried out before the oxidation step, on earlier intermediates. Enantiomers may be separated using chiral resolving agents such as L-(+)-tartaric acid, D-(+)-malic acid, gulonic acid derivatives such as 2,3:4,6-di-O-isopropylidene-2-keto-L-gulonic acid, camphorsulphonic acid, dibenzoyl tartaric acid, mandelic acid and (S)-(+)- and (R)-(–)-1,1'-binaphthyl-2,2'-diyl hydrogen phosphate, or chiral chromatography. For resolution of the compound of formula (VII) where $R_3'$ is cyano and $R_2'$ is $OCH_3$, 2,3:4,6-di-O-isopropylidene-2-keto-L-gulonic acid is particularly preferred and can achieve separation of the E/Z geometric isomers. The unwanted enantiomer obtained from the separation may be racemised by treatment with a strong base such as potassium t-butoxide and the resulting mixture of enantiomers and geometric isomers separated again to furnish the required isomer. For resolution of the compound of formula (VIII) where $R_1'$ is 3-quinuclidinyl and $R_3''$ is cyano, L-(+)-tartaric and D-(+)-malic acids are particularly preferred.

A process for resolving [R,S]-α-(methoximino)-α-(1-azabicyclo[2.2.2]oct-3-yl)acetonitrile comprises treating the racemic compound with 2,3:4,6-di-O-isopropylidene-2-keto-L-gulonic acid, separating the resolved R-(Z) isomer as the crystalline gulonate salt, optionally racemising the mother liquors with strong base and obtaining a further crop of resolved R-(Z) isomer gulonate salt by repeating the treatment process, and thereafter converting the resolved R-(Z) isomer into the free base or a pharmaceutically acceptable salt.

A process for resolving racemic [R,S-(Z)]-α-(oximino)-α-(1-azabicyclo[2.2.2]oct-3-yl)acetonitrile comprises treating the racemic compound with L-(+)-tartaric or D-(+)-malic acid, separating the resolved R-(Z) isomer as the crystalline tartrate or malate salt and thereafter converting the salt to the free base.

In the preparation of the desired R-(Z) isomer of the compound of formula (I), it is preferred to obtain the Z isomer of the intermediate compound of formula (VIII) as described above. The Z isomer of the oxime of formula (VIII) may be resolved into the desired R enantiomer before methylation of the =NOH group. It has been found that base treatment of the resolved oxime does not result in unwanted racemisation of the oxime and that methylation proceeds smoothly to the required R-(Z) isomer of the final compound.

A process for preparing [R-(Z)]-α-(methoxyimino)-α-(1-azabicyclo[2.2.2]oct-3-yl)acetonitrile or a pharmaceutically acceptable salt thereof comprises treating [R-(Z)]-α-(oximino)-α-(1-azabicyclo[2.2.2]oct-3-yl)acetonitrile with base, methylating the product and thereafter optionally forming a pharmaceutically acceptable salt.

Methylation may result in some alkylation on the oxime nitrogen to give a nitrone. Hydrolysis of the reaction mixture after methylation with aqueous base such as $K_2CO_3$ at elevated temperature for example 50°–60° C. results in removal of the nitrone side product.

Higher enantiomeric purity can be achieved, if required, by recrystallisation of the chiral salt from a suitable solvent such as water (for compounds of formula (VIII) or ethyl acetate/methanol (for compounds of formula (VII)).

The compound of formula (I) is preferably isolated in substantially pure form.

Pharmaceutically acceptable salts of the compound of formula (I) may be formed conventionally by reaction with the appropriate acid.

The compound of the present invention enhances acetylcholine function via an action at muscarinic receptors within the central nervous system and is therefore of potential use in the treatment and/or prophylaxis of dementia.

The present invention also provides a pharmaceutical composition, which comprises a compound of formula (I) or a pharmaceutically acceptable salt thereof, and a pharmaceutically acceptable carrier.

The compositions may be in the form of tablets, capsules, powders, granules, lozenges, suppositories, reconstitutable powders, or liquid preparations such as oral or sterile parenteral solutions or suspensions.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The solid oral compositions may be prepared by conventional methods of blending, filling, tabletting or the like. Repeated blending operations may be used to distribute the active agent throughout those compositions employing large quantities of fillers. Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, or hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10–60% by weight, of the active material, depending on the method of administration.

The invention also provides a method of treatment and/or prophylaxis of dementia in mammals including humans, which comprises administering to the sufferer an effective amount of a compound of formula (I) or a pharmaceutically acceptable salt thereof.

The dose of the compound used in the treatment of such disorders will vary in the usual way with the seriousness of the disorders, the weight of the sufferer, and the relative efficacy of the compound. However, as a general guide suitable unit doses may be 0.05 to 100 mg, for example 0.2 to 50 mg and such unit doses may be administered more than once a day, for example two or three times a day, so that the total daily dosage is in the range of about 0.01 to 5 mg/kg and such therapy may extend for a number of weeks or months.

Within the above indicated dosage ranges no unacceptable toxicological effects are indicated for the compound of the invention.

In a further aspect the invention provides a compound of formula (I) or a pharmaceutically acceptable salt thereof for use as an active therapeutic substance.

The invention further provides a compound of formula (I) or a pharmaceutically acceptable salt thereof, for use in the treatment and/or prophylaxis of dementia.

In another aspect the invention provides the use of a compound of formula (I) or a pharmaceutically acceptable salt thereof for the preparation of a medicament for the treatment and/or prophylaxis of dementia.

In a further aspect the invention provides a method of treatment and/or prophylaxis of dementia which comprises administering an effective amount of a compound of formula (I) or a pharmaceutically acceptable salt thereof.

The following examples illustrate the invention.

EXAMPLE 1

Preparation of [R,S-(Z)]-α-(oximino)-α-(1-azabicyclo[2.2.2]oct-3-yl)acetonitrile Method A
Stage 1 Preparation of 1-azabicyclo[2.2.2]oct-3-ylidenecyanoacetic acid A mixture of quinuclidinone hydrochloride (32 g, 0.2 mol) and cyanoacetic acid (20.2 g, 1.2 eq) in water (65 ml) was mechanically stirred until a solution resulted. This was then cooled to approx 10° C. by immersion in an ice-water bath and sodium hydroxide pellets (27.0 g, 3.4 eq) added portionwise with stirring over 1 h while maintaining the reaction temperature at 15°–25° C. with the aid of the ice-bath. The resulting solution was then stirred at approx. 20° C. for an additional 1.5 h after which time a thick suspension of the sodium salt of the product was deposited and the temperature of the mixture rose to 25° C.

Stirring was continued for another 1 h at room temperature before adding dropwise conc. HCl (37 ml) over 0.5 h while maintaining the temperature of the mixture at approx. 20° C. with external cooling. As the acid was added the suspension dissolved to give a near-solution before the free acid of the product was deposited during the latter stages of the addition. The final pH of the mixture was fine-adjusted to pH7 after which stirring was continued for another 0.5 h and the mixture then left to stand at room temperature for 48 h. It was then re-stirred while chilling to 0°–5° C. for 3 h before filtering under suction. The filter cake was washed with a little ice-cold water and then dried, first under suction and then under high vacuum at 40°–45° C. overnight. Yield: 34.0 g (90%).

NMR (250 MHz, D$_2$O) δ=2.02–2.17 (2 H, m), 2.19–2.34 (2 H, m), 3.30–3.57 (5 H, m), 4.61 (2 H, s).

Stage 2 Preparation of α-cyano-1-azabicydo[2.2.2]octane-3-acetic acid

The Stage 1 nitrile acid (20 g, 0.1 mol) was suspended in water (100 ml) and 5% Pd-C paste (type 87L, 61% moisture, 3.0 g) added. The mixture was stirred vigorously under hydrogen at atmospheric pressure for 22 h. It was then filtered through celite under suction to give a solution of the reduced nitrile acid, the identity and purity of which was checked by NMR (D$_2$O) of an evaporated aliquot. The solution of Stage 2 product was used directly for the next stage.

NMR (250 MHz, D$_2$O) δ=1.85–2.24 (4.35 H, m), 2.30–2.36 (0.65 H, m), 2.63–2.80 (1 H, m), 3.08–3.45 (5 H, m) 3.56–3.77 (1 H, m).

Stage 3 Preparation of tire compound

The Stage 2 solution was chilled with stirring to 0°–5° C. using an ice bath during which conc. HCl (19 ml, 0.24 mol) was also added over 1–2 min. A solution of NaNO$_2$ (17 g, 0.25 mol) in water (230 ml) was then added dropwise over 1 h while maintaining the temperature at 0°–5° C. An initial very pale blue solution formed which turned greenish, while evolution of gas (CO$_2$) also became quite apparent. After the addition was complete the mixture was left to stir in the ice-bath while allowing to warm slowly to room temperature overnight. An NMR (D$_2$O) of the residue from a basified and evaporated aliquot showed an E:Z mixture (approx. 1:4 ratio) of the oxime to be present. The neutral reaction mixture was stirred and basified to pH8–9 by dropwise addition of a solution of NaOH (4.17 g, 0.1 mol) in water (6 ml), over 10 min during which the zwitterionic Z-isomer of the product precipitated out. The suspension was stirred while chilling to 0°–5° C. for three hours, after which it was left to stand at this temperature overnight before filtering under suction. The filter cake was washed with a little ice-cold water before drying under suction and then under high vacuum at 40°–45° C. to afford the Example 1 title compound. Yield: 12.6 g (68%).

NMR (250 MHz, D$_2$O) δ=1.82–2.15 (4 H, m), 2.36–2.44 (1 H, m), 3.20–3.43 (5 H, m), 3.50–3.65 (1 H, m), 3.67–3.78 (1 H, m).

The mother liquor from the filtration was acidified with conc. HCl (20 ml) and then left to stand at room temperature for 18 h to convert the predominantly E-isomer present into Z-isomer. Basification to pH 8–9 with 40% aq. NaOH yielded a second crop of title compound which was similarly filtered off and dried. Yield: 2.2 g (12%).

Method B

Stage 1 Preparation of 1-azabicyclo[2.2.2]oct-3-ylidenecyanoacetic acid

40% Aqueous NaOH (370 ml, 3.7 mol) was added to a stirred suspension of 3-quinuclidinone hydrochloride (600 g, 3.7 mol) in water (300 ml) over 30 min while maintaining the temperature at 15°–25° C. The resulting mixture was then cooled to 15° C. and a solution of cyanoacetic acid (380 g, 4.5 mol) in water (150 ml) added in a steady stream over 30 min while stirring and maintaining the temperature at 15°–20° C. After the addition was complete, further 40% aq. NaOH (900 ml, 9.0 mol) was added gradually over 45 min while stirring and maintaining the temperature at 15°–20° C. The resulting reddish solution was then left to stir at ambient temperature for a further 2 h before cooling to 15° C. Seeding with authentic sodium 1-azabicyclo[2.2.2]oct-3-ylidenecyanoacetate induced crystallisation of the same, and the mixture was then chilled further to 7° C. with stirring until a thick slurry of the sodium salt was obtained. After stirring at this temperature for a further 45 min a mixture of conc HCl (725 ml) and water (725 ml) was added in a steady stream over 45 min while stirring and maintaining the temperature at 15°–20° C. After adjusting to pH7 the resulting slurry of the Stage 1 product was stirred at ambient temperature for an additional 45 min before using directly for Stage 2.

Stage 2 Preparation of α-cyano-1-azabicyclo[2.2.2]octane-3-acetic acid

10% Pd-C catalyst (type 487, dry powder, 66 g) was added to the slurry of the Stage 1 product and the mixture then stirred under hydrogen at atmospheric pressure for 65 h. It was then filtered through celite under suction to give a solution of the Stage 2 product, the identity and purity of which was checked by NMR ($D_2O$) of an evaporated aliquot. The solution was used directly for the next stage.

Stage 3 Preparation of title compound

The Stage 2 solution was chilled with stirring to 7° C. and conc. HCl (790 ml, 9.3 mol) added over 5 min. The stirred mixture was chilled back to 4° C. before adding a solution of $NaNO_2$ (360 g, 5.2 mol) in water (510 ml+60 ml washings) over 1 h while maintaining the temperature at 4°–6° C. An initial very pale blue solution formed which turned greenish, while evolution of gas ($CO_2$) also became quite apparent. After the addition was complete the mixture was left to stir at 4°–6° C. for an additional 2 h before allowing to warm slowly to room temperature overnight. An NMR ($D_2O$) of the residue from a neutralised and evaporated aliquot showed an E:Z mixture (~1:5) of the oxime to be present together with a little unreacted 3-quinuclidinone (3–4%).

The reaction mixture was stirred and 40% aq. NaOH (390 ml, 3.9 mol) added in a steady stream over 1 h while maintaining the temperature at 20°–25° C. During the addition the zwitterionic Z-oxime product precipitated out. The addition of the 40% aq. NaOH was continued until a final pH of 8–9 was obtained. The resulting suspension of Z-oxime was then chilled to 4°–5° C. with stirring and maintained at this temperature for 2 h before filtering under suction. The filter cake was washed with ice-cold water (600 ml) before leaving to suck dry overnight. The product was finally dried to constant weight at 50°–55° C. under high vacuum to afford the title compound. Yield: 455 g (68% from 3-quinuclidinone hydrochloride).

EXAMPLE 2

Preparation of [R-(Z)]-α-(oximino)-α-(1-azabicyclo[2.2.2]oct-3-yl)acetonitrile

Stage 1

To a stirred suspension of racemic zwitterionic [R,S-(Z)]-α-(oximino)-α-(1-azabicyclo[2.2.2]oct-3-yl)acetonitrile from Example 1 (20.0 g, 0.11 mol) in water (148 ml) at 35° C. was added a solution of L(+) tartaric acid (16.8 g, 0.11 mol) in water (100 ml) at 30° C. The resultant mixture was warmed to 50° C., giving a homogenous solution which was then stirred at ambient temperature for 20 h. The crystalline product was filtered off, washed with water (20 ml) then sucked dry on the filter.

Stage 2

The damp solid from Stage 1 was slurried with water (49 ml) and heated to 95° C., giving a homogenous solution. This solution was stirred at ambient temperature, and seed crystals of authentic [R-(Z)]-α-(oximino)-α-(1-azabicyclo[2.2.2]oct-3-yl)acetonitrile L-(+)-tartrate salt were added at intervals until crystallisation occurred. Stirring was continued at ambient temperature for 16 h. The crystalline product was filtered off, washed with water (8 ml) then sucked dry to give the tartrate salt in high enantiomeric purity (e.e. >99%), (2.5 g, 68%).

NMR (250 MHz, DMSO) δ=1.65 (2 H, m), 1.85 (2 H, m), 2.22 (1 H, m), 2.95–3.20 (5 H, m), 3.35 (2 H, d, J=7 Hz), 4.05 (2 H, s).

Stage 3

A slurry of [R-(Z)]-α-(oximino)-α-(1-azabicyclo[2.2.2]oct-3-yl)acetonitrile L-(+)-tartrate salt from Stage 2 (12.5 g, 38 mmol) in water (60 ml) was stirred and heated to 95° C., giving a homogenous solution. Aqueous sodium hydroxide (10M) was added to this solution in 0.5 ml portions. A graph of solution pH v volume of base added was plotted, and the end point for base addition was determined as the second rapid pH change. A total of 7.5 ml of base was added. The mixture was cooled to 0° C., then stirred at this temperature for 1.5 h. The crystalline solid was filtered off, washed with a small volume of cold water, then dried in vacuo at 60° C. to give the title compound (6.3 g, 93%) of high enantiomeric purity (e.e. >99.8%).

NMR (400 MHz, DMSO) δ=1.38 (1 H, m), 1.48 (1 H, m), 1.60 (2 H, m), 2.00 (1 H, m), 2.65–2.75 (5 H, m), 2.90–3.05 (2 H, m), 13.10 (1 H, s, br).

EXAMPLE 3

Preparation of [R,S-(Z)]-α-(methoxyimino)-α-(1-azabicyclo[2.2.2]oct-3-yl)acetonitrile Zwitterionic [R,S-(Z)]-α-(oximino)-α-(1-azabicyclo[2.2.2]oct-3-yl)acetonitrile from Example 1 (35.1 g, 196 mmol) was suspended in a mixture of DMSO (250 ml) and THF (175 ml) and stirred under nitrogen while cooling to 10° C. Potassium ten-butoxide (21.9 g, 195 mmol) was added in one lot and stirring continued for approx. 0.5 h until a yellow solution resulted. The temperature rose to reach 15° C. before dropping back with external cooling. The temperature of the solution was brought down to −1° C. using an acetone/$CO_2$ bath before a solution of methyl rosylate (36.0 g, 194 mmol) in THF (75 ml) was added dropwise over 45 min while maintaining the reaction temperature at 0°–2° C. The mixture was stirred for an additional 0.5 h at 0°–5° C. by which time a thick yellow suspension had formed. Ice-cold water (100 ml) was added and the resulting solution transferred to a separating funnel containing further water (100 ml). The mixture was extracted with EtOAc (200 ml+5×130 ml portions) and the combined extracts washed with water (3×40 ml) and then brine (20 ml+40 ml) before drying over $Na_2SO_4$. Evaporation afforded the title compound as a mobile yellow oil, 91% pure by HPLC relative assay. Yield: 29.4 g (78%).

NMR (250 MHz, CDCl₃) δ=1.40–1.55 (1 H, m), 1.58–1.80 (3 H, m), 2.07–2.20 (1 H, m), 2.60–3.14 (6 H, m), 3.20–3.34 (1 H, m), 4.08 (3 H, s).

EXAMPLE 4

Preparation of [R-(Z)]-α-(methoxyimino)-α-(1-azabicyclo[2.2.2]oct-3-yl)acetonitrile.

Method A

Resolution of [R,S-(Z)]-α-(methoxyimino)-α-(1-azabicyclo[2.2.2]oct-3-yl)acetonitrile To a solution of [R,S-(Z)]-α-(methoxyimino)-α-(1-azabicyclo[2.2.2]oct-3-yl)acetonitrile from Example 3 (105.3 mg, 0.55 mmol) in ethanol (0.1 ml) was added a solution of 2,3:4,6-di-O-isopropylidene-2-keto-L-gulonic acid monohydrate (79.7 mg, 0.27 mmol) in ethanol (0.5 ml). The resultant solution was stirred at ambient temperature, then allowed to stand for 16 h. The crystalline product was filtered off, washed with a small volume of cold ethanol then dried in vacuo at 60° C. to give the title compound as its 2,3:4,6-di-O-isopropylidene 2-keto-L-gulonate salt, (44.5 mg, 34%) in high enantiomeric purity (e.e. >97%).

NMR (250 MHz, DMSO) δ=1.20 (3 H, s), 1.32 (3 H, s), 1.38 (3 H, s), 1.40 (3 H, s), 1.60 (2 H, m), 1.78 (2 H, m), 2.16 (1 H, m), 2.75–3.15 (5 H, m), 3.20 (2 H, m), 3.85 (1 H, m), 3.95–4.10 (2 H, m), 4.05 (3 H, s), 4.20 (1 H, m), 4.66 (1 H, s).

Method B

Resolution of E/Z mixture of [R,S]-α-(methoxyimino)-α-(1-azabicyclo[2.2.2]oct-3-yl)acetonitrile Stage 1

A solution of [R,S-(E,Z)]-α-(methoxyimino)-α-(1-azabicyclo[2.2.2]oct-3-yl)acetonitrile (41 g) was dissolved in ethyl acetate (100 ml) and a solution of 2,3:4,6-di-O-isopropylidene-2-keto-L-gulonic acid monohydrate (22.5 g, 0.077 mol) in ethyl acetate (400 ml) was added. Crystallisation occurred whilst standing for 16 hours. The crystals were isolated by filtration to give the 2,3:4,6-di-O-isopropylidene-2-keto-L-gulonate salt (19.3 g, 0.041 mol, 54%).

Stage 2

A solution of [R,S-(E,Z)]-α-(methoxyimino)-α-(1-azabicyclo[2.2.2]oct-3-yl)acetonitrile in ethyl acetate (the mother liquors from the crystallisation in Stage 1), was washed with 5% aqueous potassium carbonate solution, then washed with saturated aqueous potassium carbonate solution and concentrated. The residue was dissolved in THF (ca 30 wt % solution), and potassium tert-butoxide (5 wt %) was added. After 1 hour the reaction was partitioned between ethyl acetate and 5% aqueous potassium carbonate solution. The organic phase was separated, washed (5% aq K₂CO₃), dried, filtered through silica and concentrated to give a racemic mixture.

The racemic mixture was used as a starting material for a resolution in accordance with Stage 1.

EXAMPLE 5

Preparation of [R-(Z)]-α-(methoxyimino)-α-(1-azabicyclo[2.2.2]oct-3-yl)acetonitrile monohydrochloride Method A Stage 1—Isolation of title compound as free base The salt from Example 4, Method B, Stage 1 (86 g) was dissolved in water (400 ml) and the solution made basic with saturated aqueous potassium carbonate. The solution was extracted with ethyl acetate (500 ml) and the extract washed with 5% aqueous potassium carbonate (2×100ml) then saturated aqueous potassium carbonate (2×20ml). The combined aqueous phases were extracted with a further 400 ml of ethyl acetate and the extract washed as above. The combined ethyl acetate extracts were dried over potassium carbonate and concentrated to give the free base (38 g).

Stage 2—Salt formation (title compound)

The free base from Stage 1 (63 g; 0.33 mol) was dissolved in isopropyl alcohol (500 ml) and concentrated hydrochloric acid (28 ml, 0.33 mol) was added. The mixture was diluted with ethyl acetate (1l) and the solid collected by filtration, washed with ethyl acetate (2×100 ml) and dried at ambient temperature under reduced pressure (1 mm Hg) for 4 hours to give the title compound (43.9 g).

A second crop was obtained by concentrating the mother liquor to ~250 ml and adding ethyl acetate (500 ml). This was washed and dried as above (14.3 g).

Method B

Zwitterionic [R-(Z)]-α-(oximino)-α-(1-azabicyclo[2.2.2] oct-3-yl)acetonitrile from Example 2 (6.0 g, 34 mmol) was suspended in a mixture of DMSO (42 ml) and THF (12 ml) and stirred under nitrogen whilst cooling to 7° C. Potassium tert-butoxide (3.76 g, 33 mmol) was added in one portion. The cooling bath was removed and stirring was continued for 15 min during which time a homogenous solution formed and the temperature rose to 13° C. This solution was cooled to 7° C., then a solution of methyl tosylate (6.84 g, 37 mmol) in THF (6 ml) was added dropwise whilst maintaining the reaction mixture temperature at ≦13° C. The resultant mixture was stirred at ambient temperature for 2 h, then aqueous potassium carbonate (0.2M, 30 ml) was added in one portion. The temperature rose to ca. 40° C., then was further raised to 55°–60° C. and maintained at this temperature for 2 h. The resultant solution was extracted with ethyl acetate (3×30 ml), and the combined extracts were washed with aqueous potassium carbonate (0.2M, 18 ml) and water (18 ml). Propan-2-ol (100 ml) was added and the solution evaporated to a volume of 10–20 ml. Additional propan-2-ol (60 ml) was then added and the solution again evaporated to a volume of 10–20 ml. The volume was increased to 27 ml by the addition of propan-2-ol and the solution cooled to 5° C. Concentrated hydrochloric acid (2.0 ml, 24 mmol) was added slowly with stirring, keeping the temperature below 12° C. This mixture was stirred for 15 min, then ethyl acetate (60 ml) was added portionwise. The mixture was stored at 4° C. for 16 h, then the crystalline solid was filtered off, washed with a small volume of ethyl acetate then dried in vacuo at 30° C. to give the title compound (3.1 g, 40%).

NMR (250 MHz, DMSO) δ=1.75 (2 H, m), 1.95 (2 H, m), 2.33 (1 H, m), 3.05–3.28 (4 H, m), 3.28–3.55 (3 H, m), 4.08 (3 H, s), 11.12 (1 H, s, br).

| Abbreviations: | |
| --- | --- |
| DMSO | dimethyl sulphoxide |
| THF | tetrahydrofuran |
| EtOAc | ethyl acetate |

EXAMPLE 6

Synthesis of [R-(Z)]-α-(methoxyimino)-α-(1-azabicyclo[2.2.2]oct-3-yl)acetonitrile-1-oxide (Compound X)

Method A

The title compound X was prepared by a modification of the method reported by Kenyon et al (1). A solution of meta-chloroperoxybenzoic acid (MCPBA) was prepared by dissolving 377 mg of MCPBA in 100 ml of dichloromethane (DCM). This solution was added to an ice-chilled solution of [R-(Z)]-α-(methoxyimino)-α-(1-azabicyclo[2.2.2]oct-3-yl) acetonitrile monohydrochloride (Example 5) (398 mg) in DCM (100 ml). The mixture was left at room temperature overnight before placing at approximately +4° C. A further 323 mg of MCPBA in 100 ml DCM was added some days later. After 2 hours at room temperature, 100 ml of Milli-Q water was added to the reaction vessel and the flask shaken vigorously. The DCM layer was separated and re-extracted with approximately 100 ml of Milli-Q water. The aqueous phases were combined, freeze-dried and crudely purified using HPLC prior to re-lyophilization. The freeze-dried sample was re-dissolved in a total of approximately 15 ml of Milli-Q water and centrifuged (2.5 mins, high speed, MSE Microcentaur). Aliquots of the supernatant were then chromatographed using the semi-preparative HPLC method described below.

| HPLC: | Gilson HPLC system, 715 HPLC controller software, Version 1.0 |
| --- | --- |
| | Jasco 875 UV Detector, 240 nm, referenced against air |
| Column: | Waters µBondapak C-18 Semi-Prep, 30 cm × 10 mm ID |
| Column Temperature: | Ambient |
| Mobile Phase: | A: Milli-Q water |
| | B: Acetonitrile |
| Flow rate: | 4.0 ml. min$^{-1}$ |
| Injection Volumes: | approximately 4000–5000 µl |
| Solvent Conditions: | Time (min) % A |

| Time (min) | % A |
| --- | --- |
| 0 | 100.0 |
| 8 | 100.0 |
| 33 | 0.0 |
| 37 | 100.0 |
| 45 | 100.0 |

The fractions containing the peak of interest were pooled, evaporated to dryness (nitrogen stream followed by freeze-drying). The resulting solid residue was analysed by nuclear magnetic resonance, infra-red, mass spectroscopy and elemental analysis. The overall yield of title compound was approximately 57%.

(1) G. L. Kenyon, D. H. Eargle, Jr and C. W. Koch, J. Org. Chem., 41, 2417, 1976

Analysis

| | Expected: | Found: |
| --- | --- | --- |
| C: | 57.4% | 52.36%–52.55% |
| H: | 7.23% | 7.24%–7.29% |
| N: | 20.08% | 18.31%–18.35% |

NMR: $^1$H, DMSO-d$^6$ 360.13 MHz ppm; 1.73–1.92 (M, 2 H), 1.95–2.06 (M, 2 H), 2.13–2.20 (M, 1 H), 2.99–3.10 (td, 1 H), 3.13–3.23 (M, 2 H), 3.29—ca 3.51 (M, ≅4 H), 4.08 (S, 3 H) 9.7 mg/0.7 ml DMSO $^{13}$C, DMSO—d$^6$ 90.56 MHz ppm132.00, 109.86, 63.85, 62.69, 62.35, 62.25, 39.00, 25.44, 23.71, 21.61 30 mg/0.7 ml DMSO

MS: M+H$^+$=210

Method B

To a stirred and ice-chilled solution of [R-(Z)]-α-(methoxyimino)-α-(1-azabicyclo[2.2.2]oct-3-yl)acetonitrile monohydrochloride (Example 5) (15 g) in dichloromethane (600 ml) was added, in portions over 3.5 h, meta-chloroperoxybenzoic acid (26 g). After the reaction was judged to be complete (thin layer chromatography: neutral Al$_2$O$_3$—3% methanol/dichloromethane) the mixture was left to stand at 0°–5° C. for 18 h during which meta-chlorobenzoic acid was deposited. This was filtered off under suction, and the filtrate concentrated down to a small volume (c.a. 100 ml) which induced further crystallisation of meta-chlorobenzoic acid. This was also filtered off, and the resulting clear yellow filtrate then subjected to alumina column chromatography (eluent: 3–5% methanol/dichloromethane) to remove residual meta-chlorobenzoic acid and minor impurities. The fractions containing the title compound were combined and concentrated down to a very small volume before ethyl acetate was slowly added to induce crystallisation. After leaving for 1 h, further evaporation to remove residual dichloromethane induced additional crystallisation, and the mixture was left to stand at room temperature overnight to complete the process. The hygroscopic crystalline material was filtered off under suction, and washed with a little ethyl acetate before drying under suction in a dry nitrogen atmosphere. It was finally dried under vacuum at 35°–40° C. (Yield: 6.2 g; 45%).

NMR (CDCl$_3$) δ: 1.95–2.06 (m, 2 H), 2.10–2.25 (m, 2 H), 2.38–2.45 (m, 1 H), 3.20–3.30 (m, 1 H), 3.35–3.58 (m, 5 H), 3.98 (dr, 1 H), 4.14 (s, 3 H).

Biological Activity

Materials and Methods

Ligand Binding Studies in vitro

Cerebral cortex was dissected from male Hooded Lister rats (Olac, U.K.) into 2.5 volumes (compared with wet weight) ice cold 50 mM tris pH 7.7. This was homogenised and then centrifuged at 24,000 g for 15 minutes at 4° C. The pellet was resuspended in 2.5 volumes of fresh, cold buffer and washed twice more. The final resuspension was in 2.5 vols and the homogenates were stored in 1 ml aliquots at −20° C. until required.

Incubations for [$^3$H]-oxotremorine-M ([$^3$H]-OXO-M) binding were prepared in a total volume of 2 ml of ice cold 50 mM Tris, containing 2 mM magnesium chloride. [$^3$H]-OXO-M acetate (New England Nuclear, specific activity 87 Ci/mmol) was added to a concentration of 1.88 nM. Cortex homogenate was at a final concentration of 300 vols based on the original wet weight (equivalent to 0.145 mg protein/ ml). Non-specific binding was defined using 10 µM oxotremorine sesquifumarate. Incubations were carried out to equilibrium at 37° C. for between 30 and 45 mins. Samples were filtered through Whatman GF/B filters pre-soaked for 30 minutes in a 0.05% aqueous solution of polyethylenimine to prevent adsorption of [$^3$H]-OXO-M to the glass fibre.

[$^3$H]-Quinuclidinyl benzilate ([$^3$H]-QNB, specific activity 44 Ci/mmol, final conc. 0.27 nM) binding was carried out similarly except that the magnesium chloride was omitted and the dilution of the homogenate was increased to 1500 vols (7.8 µg protein/ml). Non-specific binding was defined with 1 µM atropine sulphate.

Functional Studies in vivo

Male mice (CD1, Charles River UK, 25–35 g) were used in the in vivo experiments. Animals were housed in groups of 10 and allowed food and water ad libitum. Two hours prior to the experiment the animals were rehoused in groups of 5 and allowed to acclimatize to their new environment. Each group was assigned one dose of test compound.

Test compounds or vehicle were administered by either the subcutaneous (sc) or oral (po) routes. Animals were subjectively assessed for signs of salivation and body tremor 15, 30, 45, 60, 90, 120, 150, 180, 240 and 300 minutes post dose, using a scoring system: 0=absent; 1=mild; 2=moderate; 3=severe. Changes in core body temperature, a measure of central activity, were recorded at the same timepoints using a rectal probe (Comark Electronic Thermometer Type 9001 )

TABLE 1

Inhibition of Ligand Binding

| Compound | [$^3$H]-OXO-M IC$_{50}$ (cortex) | n | [$^3$H]-QNB IC$_{50}$ (cortex) | n | Ratio IC$_{50}$'s QNB/OXO-M |
|---|---|---|---|---|---|
| Compound X | 2862.7 | 2 | 68747.8 | 2 | 24.0 |

IC$_{50}$ values (nM) against [$^3$H]-OXO-M and [$^3$H]-QNB in rat cerebral cortex
− geometric mean ± SEM
n = number of experiments

TABLE 2

Summary of the effects of Compound X in the mouse, after sc and po administration

| Route of administration | Salivation ED$_{50}$ (95% CL) | Hypothermia ED$_{3°}$ (95% CL) | Tremor ED$_{50}$ (95% CL) |
|---|---|---|---|
| Subcutaneous | 2.38 (1.85–3.06) | 21.3 (10.5–43.2) | >30.0 |
| Oral | <0.3 | 5.8 (4.2–8.0) | >30.0 |

ED50 Dose inducing 50% of the maximum score (mg kg$^{-1}$)
ED3° Dose inducing 3° fall in core body temperature (mg kg$^{-1}$)
95% CL 95% confidence limits

We claim:

1. A compound of formula (I) or a pharmaceutically acceptable salt thereof:

$$R_1 \overset{N-R_2}{\underset{R_3}{\bigg\langle}} \qquad (I)$$

wherein R$_1$ represents

[structure: 1-azabicyclo[2.2.2]oct-3-yl N-oxide]

R$_2$ is a group OCH$_3$, and
R$_3$ is cyano.

2. [R-(Z)]-α-(methoxyimino)-α-(1-azabicyclo[2.2.2]oct-3-yl)acetonitrile-1-oxide or a pharmaceutically acceptable salt thereof.

3. A compound according to claim 1 in pharmaceutically acceptable form.

4. A compound according to claim 2 in pharmaceutically acceptable form.

5. A compound according to claim 1 in substantially pure form.

6. A compound according to claim 2 in substantially pure form.

7. A pharmaceutical composition, which comprises a compound according to claim 1 and a pharmaceutically acceptable carrier.

8. A pharmaceutical composition, which comprises a compound according to claim 2 and a pharmaceutically acceptable carrier.

9. A method of treatment and/or prophylaxis of dementia which comprises administering an effective amount of a compound according to claim 1.

10. A method of treatment and/or prophylaxis of dementia which comprises administering an effective amount of a compound according to claim 2.

11. A process for the preparation of a compound of formula (I) as defined in claim 1, or a pharmaceutically acceptable salt thereof, which process comprises:

(a) reacting a compound of formula (II):

$$R_1' \overset{O}{\underset{R_3'}{-\!\!\!\bigg\langle}} \qquad (II)$$

with a compound of formula (III):

$$R_2'-NH_2 \qquad (III)$$

wherein R$_2$' represents R$_2$ or hydroxy, and R$_1$' and R$_3$' represent R$_1$ and R$_3$ or groups convertible thereto, and thereafter converting R$_2$' to R$_2$ when hydroxy, and converting R$_1$' and R$_3$' when other than R$_1$ and R$_3$ to R$_1$ and R$_3$, wherein R$_1$, R$_2$ and R$_3$ are as defined in formula (I);

(b) reacting a compound of formula (IV):

$$R_1' \overset{N^{R_2}}{\underset{Cl\, or\, Br}{-\!\!\!\bigg\langle}} \qquad (IV)$$

wherein R'$_1$ is R$_1$ or a group convertible thereto, with a compound of formula (V):

$$M-R_3 \qquad (V)$$

capable of generating an R$_3$ nucleophile, and thereafter converting R$_1$' when other than R$_1$ to R$_1$, wherein R$_1$, R$_2$ and R$_3$ are as defined in formula (I);

(c) nitrosating a compound of formula (VI):

$$R_1'\frown R_3" \qquad (VI)$$

wherein R$_1$' is R$_1$ or a group convertible thereto, and R$_3$" is an electron withdrawing group, and thereafter converting the resulting =NOH group to =NR$_2$ and converting R$_1$' and R$_3$" when other than R$_1$ and R$_3$ to R$_1$ and R$_3$, wherein R1, R$_2$ and R$_3$ are as defined in formula (I);

(d) reacting a compound of formula (X):

$$R_1' \overset{CO_2H}{\frown} R_3" \qquad (X)$$

wherein R$_1$' is R$_1$ or a group convertible thereto, and R$_3$" is an electron withdrawing group, with a source of nitrous acid and thereafter converting the resulting =NOH group to =NR$_2$ and converting R$_1$' and R$_3$" when other than R$_1$ and R$_3$ to R$_1$ and R3, wherein R$_1$, R$_2$ and R$_3$ are as defined in formula (I); or (e) oxidising a compound of formula (VII):
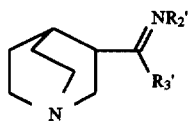
(VII)
wherein $R_2'$ and $R_3'$ are $R_2$ and $R_3$ or groups convertible thereto and thereafter converting $R_2'$ and $R_3'$ when other than $R_2$ and $R_3$ to $R_2$ and $R_3$ as defined in formula (I); and thereafter optionally forming a pharmaceutically acceptable salt.
* * * * *